United States Patent [19]

Bryce et al.

[11] Patent Number: 5,702,253
[45] Date of Patent: Dec. 30, 1997

[54] PERSONALITY TESTING APPARATUS AND METHOD

[76] Inventors: Nathan K. Bryce, P.O. Box 15935, Phoenix, Ariz. 85060; Russell R. Kesterson, 3801 E. Lincoln Dr., Paradise Valley, Ariz. 85253

[21] Appl. No.: 416,084

[22] Filed: Jul. 10, 1995

[51] Int. Cl.⁶ .................................................. G09B 19/00
[52] U.S. Cl. ............................................................. 434/236
[58] Field of Search .................................... 434/236, 106, 434/129, 155; 273/161, 296, 304, 303, 308

[56] References Cited

U.S. PATENT DOCUMENTS

| | | | |
|---|---|---|---|
| 746,750 | 12/1903 | Seymour | 273/304 |
| 1,370,249 | 3/1921 | White | 273/161 |
| 1,540,085 | 6/1925 | Partridge | 273/304 |
| 1,583,223 | 5/1926 | Cooke | 273/308 |
| 2,034,991 | 3/1936 | Salinger | 273/161 |
| 4,294,451 | 10/1981 | Wollner | 273/304 |
| 4,583,737 | 4/1986 | Falcone et al. | 273/161 |
| 4,728,108 | 3/1988 | Neuwahl | 273/296 |
| 4,779,870 | 10/1988 | Nichols | 273/161 |

*Primary Examiner*—Paul J. Hirsch
*Attorney, Agent, or Firm*—Schmeiser, Olsen & Watts

[57] ABSTRACT

The invention is a process and apparatus for determining a person's basic personality type. The apparatus includes a card deck having forty different testing cards with each card featuring a written description of a personality characteristic, an associated picture and one of four different color codes associated with a particular type of personality having that characteristic. Five pile labeling cards are also provided. The pile labeling cards are used to define separate pile areas into which the testing cards may be sorted based upon the degree to which the person agrees with the characteristic described on the testing card. A point value is given to each testing card depending on which of the piles it is placed in. The point values of the sorted testing cards are then added together relative to their color codes to determine the user's primary personality type.

10 Claims, 3 Drawing Sheets

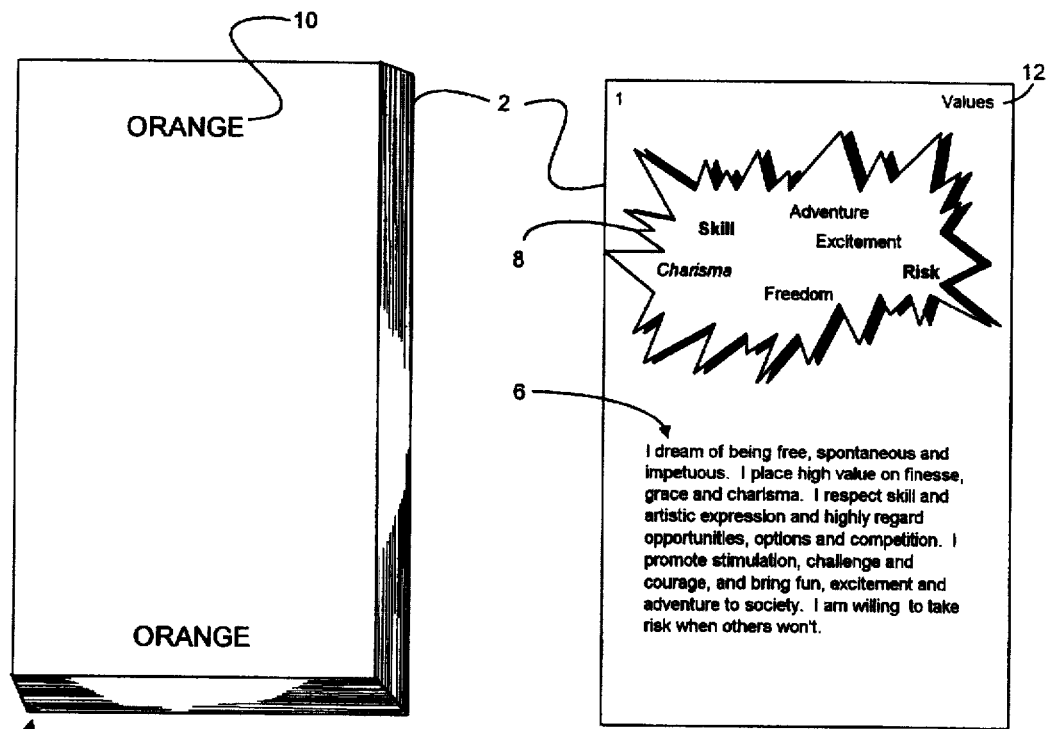
FIGURE 1
FIGURE 2
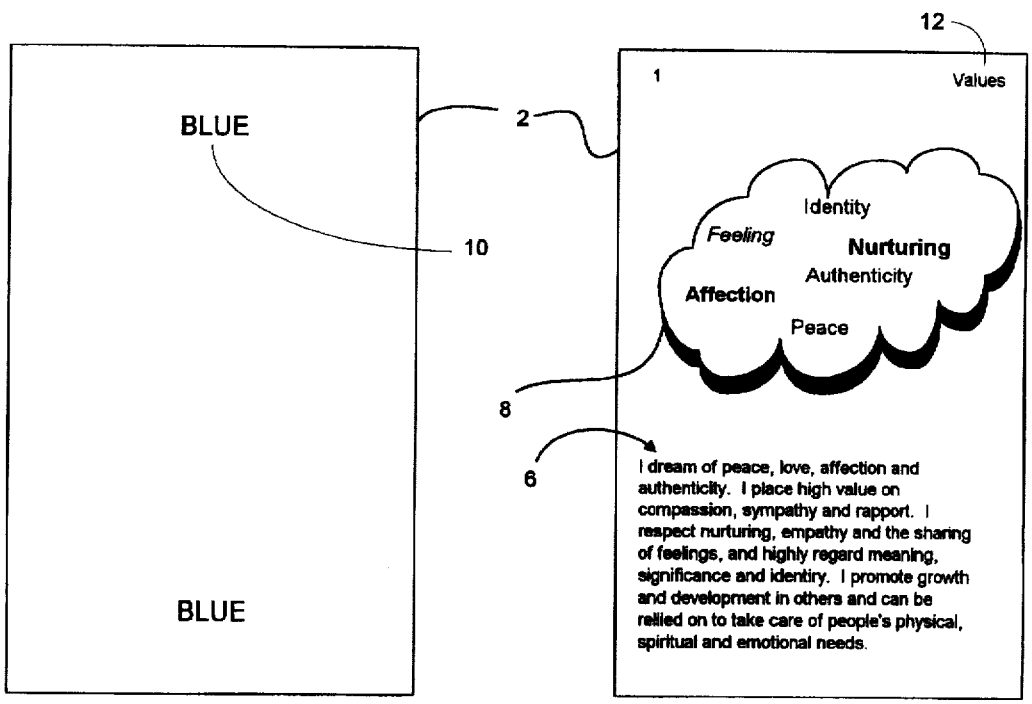
FIGURE 3
FIGURE 4

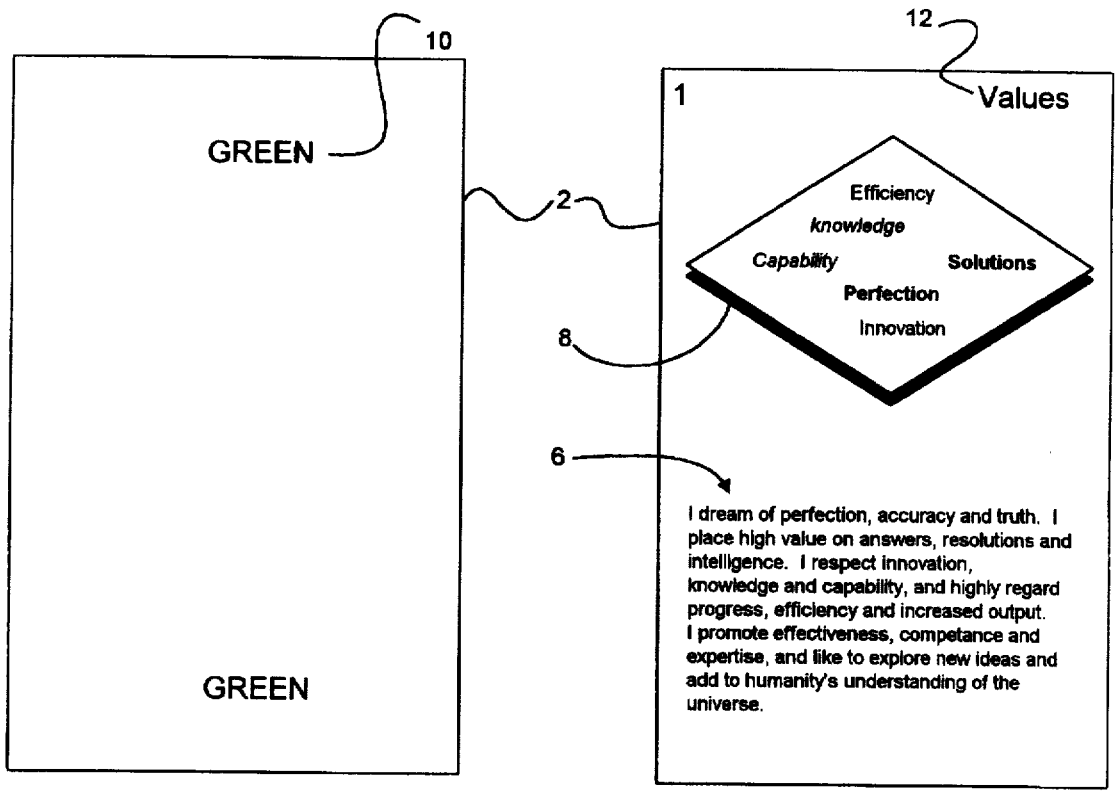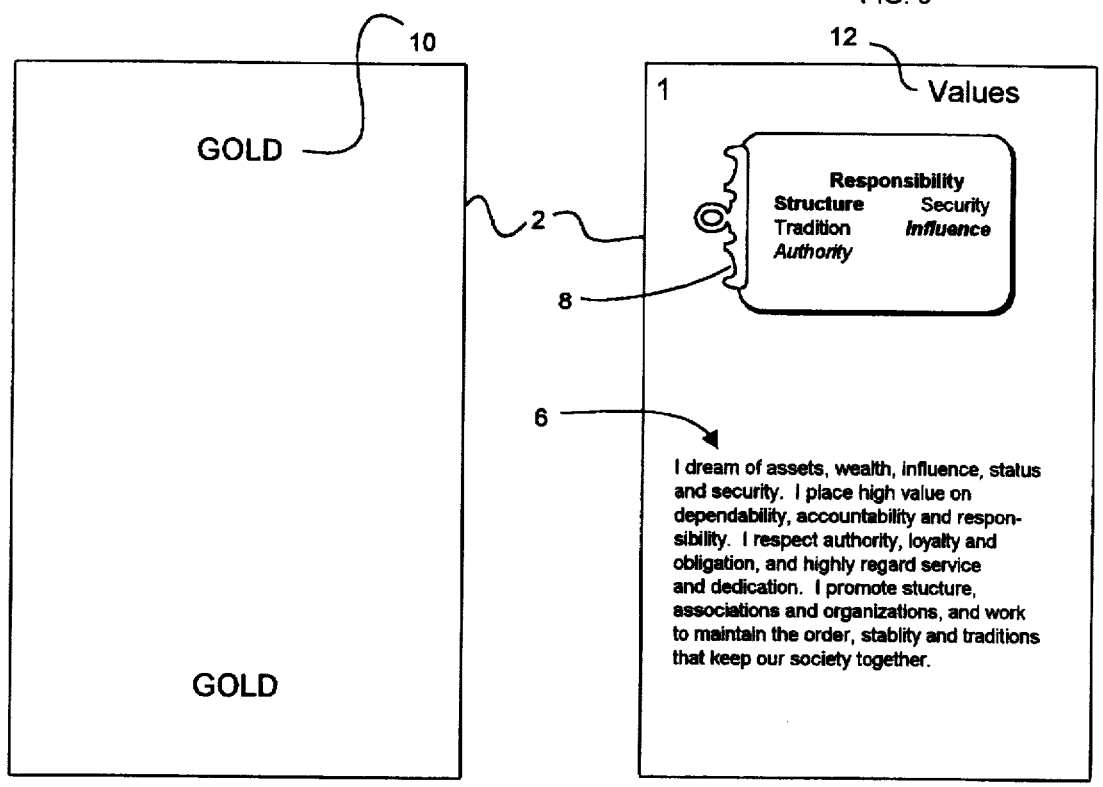

PERSONALITY TESTING APPARATUS AND METHOD

FIELD OF THE INVENTION

The invention is in the field of procedures and apparatus for psychological testing. More particularly, the invention is a procedure and apparatus designed to facilitate the identification of a person's basic personality. The apparatus employs a large number of different cards that include testing and coding indicia relative to four different basic personality types.

BACKGROUND OF THE INVENTION

Personality testing is a common practice for helping an individual to determine a proper vocation or to further understand his or her own motivations or feelings. Testing is normally accomplished by having the individual answer a series of questions relative to certain broad categories of activities, emotions, motivations or goals. The individual's responses are then correlated and a general personality pattern is identified.

The Myers-Briggs Personality Inventory and the Herman Brain Dominance Instrument are well known teachings in the personality testing field in which specific groupings of characteristics are identified with four basic personality types. As a standard practice in the testing field, each personality type is labeled with a particular color.

The first personality type is identified as a "gold" personality. This type of person is usually highly-structured, authoritative and responsible.

The second personality type is associated with the color green. A "green" personality is competent, inventive, naturally skeptical and is continually in the pursuit of knowledge.

The third personality type is identified as a "blue" personality. This type of person is people-oriented and imaginative.

Lastly, the fourth personality type is associated with the color orange. An "orange" person is adventurous and action-oriented.

Current methods of psychological testing try to determine a person's primary personality "color" by analyzing the person's responses to a large number of indicator questions. The strength of the response provides insight into the strength of that particular personality characteristic in the individual. After a large number of questions have been answered, the answers are scored and then a final tabulation based on point totals for each "color" is made. The final result will normally clearly indicate the basic and ancillary personality "colors" of the individual.

The current methodology used for personality testing groups the questions by "color" and the individual sequentially answers four separated groups of questions. Each group of questions is shown with its particular "color" and is spaced-apart or otherwise separated from the other groups of questions.

This methodology is responsible for a number of problems that may affect the test's accuracy. When presented with a group of questions of a known "color," an individual may provide a response that is tainted by how the individual would like to be instead of how the individual actually is. For example, when an individual sees a list of questions that are all on one sheet and are identified with a particular color, the individual may wish to think of himself as, for example, daring and adventurous and he will then answer the "orange" questions more strongly than is really true.

A second problem that occurs when grouping questions is that when determining the final score based on strength of response, the answers provided for the first group of questions may be much weaker or stronger than provided for the last group of questions. This may happen simply because the individual becomes more comfortable with the testing process over time. A possible result is that the test's results may be significantly affected by the order in which the individual answers each group of questions.

A third problem occurs during the tabulation stage of the testing procedure. At this stage, the responses to the questions are weighted based on the strength of the individual's response and then are added together by "color." The possibly great variation of response strength that an individual may feel for different ones of the questions may make the tabulation process extremely onerous and time-consuming.

SUMMARY OF THE INVENTION

The invention is a process and apparatus for personality testing. The apparatus is primarily in the form of a deck of specially-designed cards. The deck includes forty testing cards that have, on each one, a different written statement describing a particular personality trait or indicator thereof. Each testing card further includes a picture that would typically be associated with the particular written statement. For example, a card having a romantic statement might also display a picture of a heart. The written statement and picture are both located on the front face of the card.

The back face of each card displays a "color" indicator. The "color" indicator is used to classify the card with one of the four previously-described personality "colors." It should be noted that when an individual is looking at the front face of the card and reading the written statement or looking at the picture, the card's "color" indicator is not viewable.

The card deck preferably also includes five stack labeling cards. The labeling cards are used to define separate piles or areas into which the testing cards are sorted. Each labeling card includes written indicia that indicates to a user that the pile labeled with the labeling card should be associated with a particular degree or strength of agreement the user has for the written statement of the testing card being considered. One of the labeling cards indicates full agreement, three indicate degrees of partial agreement and one indicates total disagreement. As each testing card is read, the person considers its written statement and then places it into the appropriate one of the piles as defined by the labeling cards. By spreading out the labeling cards and then stacking the testing cards atop or proximate these cards using the agreement criteria, a person will effectively sort the cards in a manner that will lead to the indication of the user's "color."

Each labeling card preferably also includes a number that indicates a point value that should be given to each card that is placed into the associated pile. For example, each card in the "full agreement" pile is given four points, each card in the next pile is given three points and so on. After the person has read each testing card and placed it in the appropriate pile, his or her personality is analyzed by noting which cards are in which of the labeled piles and then tabulating the numerical score for each personality "color." The tabulation is accomplished by noting the point value of each card (as determined by which pile it is located in) and the "color" of the card. After the tabulation process is complete, the "color" that has the highest point total is then considered to be the person's primary personality type. The secondary, tertiary, etc. "colors" are then noted as being major or minor influences on the user's primary personality. This data helps a user to understand his or her primary motivations, needs and capabilities.

By providing a testing system in which the user answers a number of questions without being influenced by their order or "color," the invention significantly enhances the resultant accuracy of the test compared to the prior art. In addition, the manner in which the system yields a plurality of separate piles of cards with each particular pile determining the point value of any cards stacked thereon greatly facilitates the tabulation process. As a result, the testing system may be employed to quickly, accurately and easily determine a person's personality type.

BRIEF DESCRIPTION OF THE DRAWINGS

FIG. 1 shows a deck of testing cards in accordance with the invention.

FIG. 2 shows the front face of the top card shown in FIG. 1.

FIG. 3 shows the back face of a second one of the testing cards in accordance with the invention.

FIG. 4 shows the front face of the card shown in FIG. 3.

FIG. 5 shows the back face of a third one of the testing cards in accordance with the invention.

FIG. 6 shows the front face of the card shown in FIG. 5.

FIG. 7 shows the back face of a fourth one of the testing cards in accordance with the invention.

FIG. 8 shows the front face of the card shown in FIG. 7.

DETAILED DESCRIPTION OF THE DRAWINGS

Figure 9:
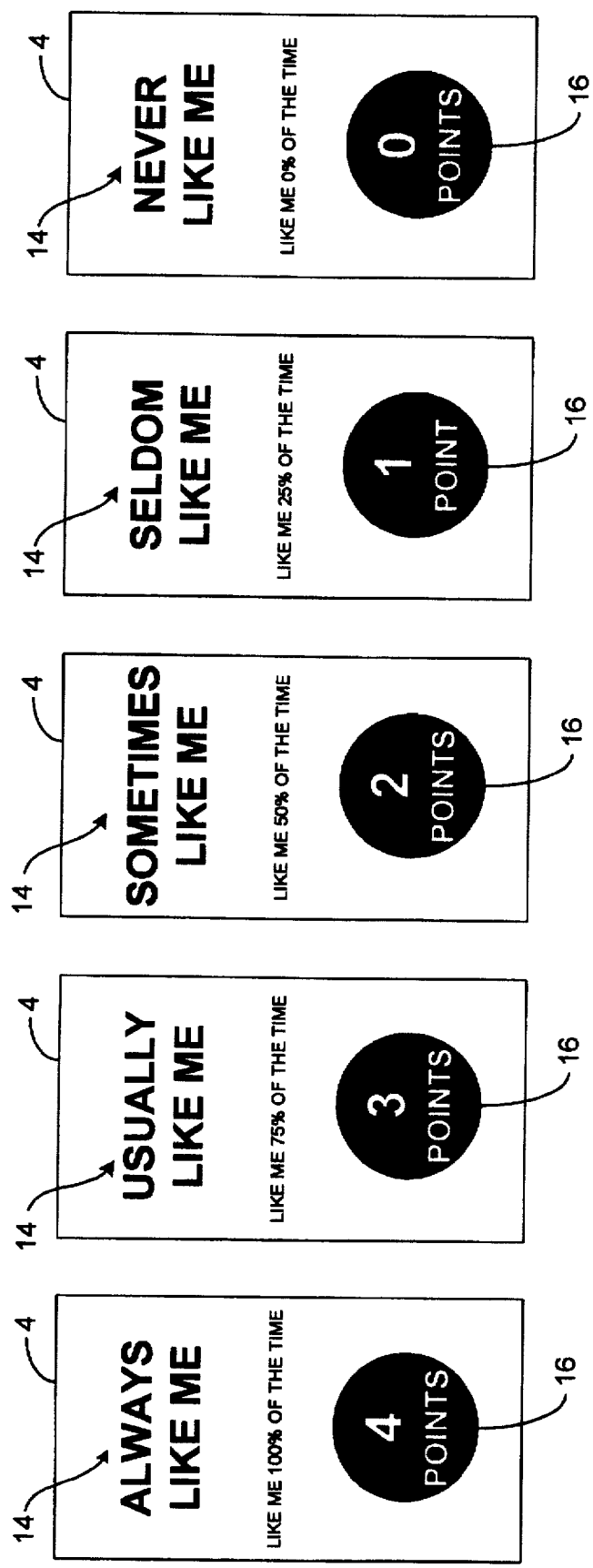
FIG. 9 shows the front face of five labeling cards in accordance with the invention.

Referring now to the drawings in greater detail, wherein like reference characters refer to like parts throughout the several figures, there is shown by the numeral 1 a deck of personality testing cards in accordance with the invention.

The deck 1 preferably includes forty testing cards 2 and five stack labeling cards 4. The front face of each card 2 has a written statement 6 that describes a personality trait or personality indicator. A picture 8 associated with the card's written statement is also located on the front face of each card. It should be noted that each card has a different written statement and picture.

The back face of each card has a "color" indicator 10 that either in words or in color indicates one of the four basic personality "colors" (blue, gold, orange, green) associated with the previously-described four basic personality types. The color indicator 10 of each card is associated with the written statement shown on the card's front face. For example, the top card shown in FIG. 1 has an "orange" indicator which is the personality "color" that would be given to an individual who is described by the written statement 6 and picture 8 shown in FIG. 2. Similar examples are provided in FIGS. 3–8.

The forty testing cards include ten cards having "orange" indicators, ten having "gold" indicators, ten having "blue" indicators and ten having "green" indicators. In addition, the forty cards are also divided into ten different categories. Four cards, one in each of the four "colors," are included in each category.

The top card in FIG. 1 and the three cards shown in FIGS. 3–8 are all in the same "values" category. The written statements shown apply to different values that are indicative of the card's associated personality "color". As shown, each card has a secondary indicia 12 that describes the category classification of the card. In the preferred embodiment, the other categories are: motivation, communication, work, supervision, recreation, childhood, youth, education and love.

FIG. 9 shows the five stack labeling cards 4. The front face of each card has indicia 14 that represents an amount of agreement. As shown, the amount of agreement varies from full agreement (Always Like Me), to three levels of partial agreement to complete disagreement (Never Like Me).

The labeling cards are used to define separate card piles upon which the testing cards 2 will be stacked during the analysis testing procedure. In addition to indicia 14, each labeling card has an indicia 16 that denotes the point value that will be given to each testing card that is placed in the particular labeled pile. For example, each testing card placed in the pile defined as "Always like me" (full agreement) will be given four points. As shown, each pile has its own particular point value.

It should be noted that the five labeling cards may be the same size as the basic cards 2 and be included in the deck 1, or they may be larger or smaller in size and form a second deck that will be used in combination with deck 1. It should also be noted that neither the front face nor the back face (not shown) of the stack labeling cards has any "color" indicator since these cards are not associated with any particular personality type.

The process or method of personality testing in combination with the taught apparatus will now be described.

The first step is for the user to identify the five labeling cards 4 and lay them out on a flat surface where they are spaced apart from each other. The cards are oriented so that their indicia 14 and 16 is face up and easily readable.

The next step is for the user to take the main deck 1 of testing cards and sort the cards by their category indicia 12. Next, the user picks a first category and lays out the four testing cards in that category in a face-up orientation. The user reads the written statement and/or looks at the picture on each card and decides on the strength of his or her agreement or identification with the statement and/or picture. After this decision is made for each card, the user places the card atop or adjacent the appropriate one of cards 4 that describes his or her degree of agreement with the card's statement/picture. This process is continued with each succeeding card category until all forty of the cards have been placed into piles defined by the labeling cards 4. It should be noted that the user does not look at the back face of the testing cards 2 during this part of the process.

As an alternate to the above-described procedure where the testing cards are ordered by category, the user can shuffle the testing cards and look at them one at a time in a random fashion. Each card is then placed in the appropriate labeled pile based on level of agreement as previously described.

The next step in the testing process is to analyze the user's personality by determining/tabulating the total points for each "color." This is achieved by turning over each stack of testing cards and counting the number of cards you have of each color (using the color indicator 10 on the back of each testing card). That number is then multiplied by the value of each stack (per indicia 16 of the associated labeling card). For example, if the "full agreement" pile had six cards of which four were blue, one was green and one was orange, the pile would be tabulated as having sixteen points for blue, four points for green and four points for orange.

After each of the piles has been analyzed, the points are added together by color to thereby determine the total points for each color. The color having the highest point score is the user's basic personality "color." The "color" having the second highest score is considered to be the user's secondary personality type and is considered to somewhat influence the user's basic personality.

As a second embodiment and alternate to the above-described methodology, the individual looks at the front face of each card and, if the card describes the individual, the card is kept. If the card does not describe the individual, it is discarded. After all forty testing cards have been viewed, the person looks at the cards that have not been discarded and counts the number of cards of each "color." The color having the greatest number is the individual's primary personality-type "color."

The embodiments disclosed herein have been discussed for the purpose of familiarizing the reader with the novel aspects of the invention. Although preferred embodiments of the invention have been shown and described, many changes, modifications and substitutions may be made by one having ordinary skill in the art without necessarily departing from the spirit and scope of the invention as described in the following claims.

We claim:

1. An apparatus for personality testing, said apparatus comprising:

a card deck having a plurality of testing cards, each of said cards having a top face upon which is located a written statement of a personality characteristic and wherein each card also has a bottom surface having an identifier that identifies the card as being from one of four different color groups, said top and bottom surfaces being opposed to each other such that a person being tested cannot see the color identifier when viewing the top surface thereby avoiding any prejudicial effect; and a plurality of labeling cards, wherein each of said labeling cards is used to label an area upon which said testing cards may be placed and wherein each labeling card includes a first indicia that describes a degree of strength of agreement a user may have with the written statements provided on the testing cards, and wherein all of the labeling cards have different first indicia, said labeling cards also having a second indicia that describes a numerical point value that should be given to any of said testing cards that are placed into an area associated with said labeling card and wherein all of said labeling cards have different second indicia such that after a numerical value is given to each card the value of cards of the same color can be added and compared to the numerical total of other color groups.

2. The apparatus of claim 1 wherein the card deck includes forty different testing cards and wherein ten of said testing cards include an identifier associated with a first color, ten of said testing cards include an identifier associated with a second color, ten of said testing cards include an identifier associated with a third color and ten of said testing cards include an identifier associated with a fourth color and wherein each of said first, second, third and fourth colors are different from each other.

3. The apparatus of claim 1 wherein the labeling cards are devoid of any indicia designed to be associated with any of said four color groups.

4. The apparatus of claim 1 wherein each testing card also includes a picture located on its front face with said picture showing an image related to the card's written statement. the color indicator of each card and the card's point value based upon which of said piles it is located in and wherein the basic personality type having the greatest number of points is considered to be the user's primary personality type.

5. The invention of claim 1 wherein each card has a secondary indicia on its top face that provides a category classification of the card, such that the person being tested can view all of the cards in a particular category prior to placing them in association with the chosen labeling cards.

6. A method for testing and determining a person's basic personality type, said method comprising:

(a) a testing person taking a first card from a specially-designed deck and then reading a written statement located on a front face of said card to a person being tested, wherein said statement describes a characteristic associated with one of four basic personality types, and wherein said card also includes a color indicator associated with the basic personality type associated with the card's written statement;

(b) the testing person receiving an answer to the question from the person being tested, the person being tested answering according to (deciding) the degree to which the written statement describes the (user) person being tested;

(c) the testing person placing the first card onto one of a plurality of piles with each pile being associated with a different degree of agreement and a different point value;

(d) repeating the above-described procedure with every card in the deck; and (e) the testing person evaluating the (user's) personality type by tabulating the total points for each basic personality type as determined by the color indicator of each card and the card's point value based upon which of said piles it is located in and wherein the basic personality type having the greatest number of points is considered to be the (user's) primary personality type of the person being tested.

7. The method of claim 6 wherein each card also includes a picture associated with the card's written statement and wherein when a user looks at the card, the user also sees the card's picture.

8. The method of claim 6 further comprising an initial step of laying out a plurality of labeling cards that function to label a plurality of different piles onto which the cards from the deck are sorted.

9. The method of claim 6 wherein each card has a secondary indicia that provides a category classification of the card, said method including the testing person showing the person to be tested the characteristic statements on all cards with the same category classification prior to placing each of the cards onto one of a plurality of piles.

10. The method of claim 6 wherein the testing person and the person being tested are the same person.

* * * * *